United States Patent [19]

Somerson et al.

[11] Patent Number: 5,669,379
[45] Date of Patent: Sep. 23, 1997

[54] WAVEFORM DISPLAY FOR MEDICAL VENTILATOR

[75] Inventors: Steven K. Somerson, Madison; Kevin G. Tissot, Brooklyn; James R. Homuth, DeForest, all of Wis.

[73] Assignee: Ohmeda Inc., Liberty Corner, N.J.

[21] Appl. No.: 624,066

[22] Filed: Mar. 29, 1996

[51] Int. Cl.$^6$ ......................................................... A61B 5/08
[52] U.S. Cl. ................... 128/204.21; 128/204.18
[58] Field of Search .................. 128/204.21, 204.22, 128/204.23, 204.24, 716

[56] References Cited

U.S. PATENT DOCUMENTS

| | | | |
|---|---|---|---|
| 4,972,842 | 11/1990 | Korten et al. | 128/716 |
| 5,520,192 | 5/1996 | Kitney et al. | 128/716 |

*Primary Examiner*—Vincent Millin
*Assistant Examiner*—Robert N. Wieland

*Attorney, Agent, or Firm*—Roger M. Rathbun; Salvatore P. Pace

[57] ABSTRACT

An algorithm is disclosed that enables the display for a medical ventilator to automatically adjust its wave characteristics depending on the settings for that ventilator established by the clinician. As the respiratory rate, or rate at which the ventilator provides breaths to the patient, is changed by the user, the rate of sweep of the waveform generator displaying that data is also changed to insure that the data is displayed in the most relevant manner. As another parameter, as the pressure limit in the patient circuit is set by the clinician, the waveform vertical scale is adjusted to make sure the particular limit of pressure is displayed. As the pressure limit or the respiratory rate are changed in the ventilator by the clinician, the waveform of he data displayed also is automatically modified to make that data best presentable to the clinician.

13 Claims, 1 Drawing Sheet

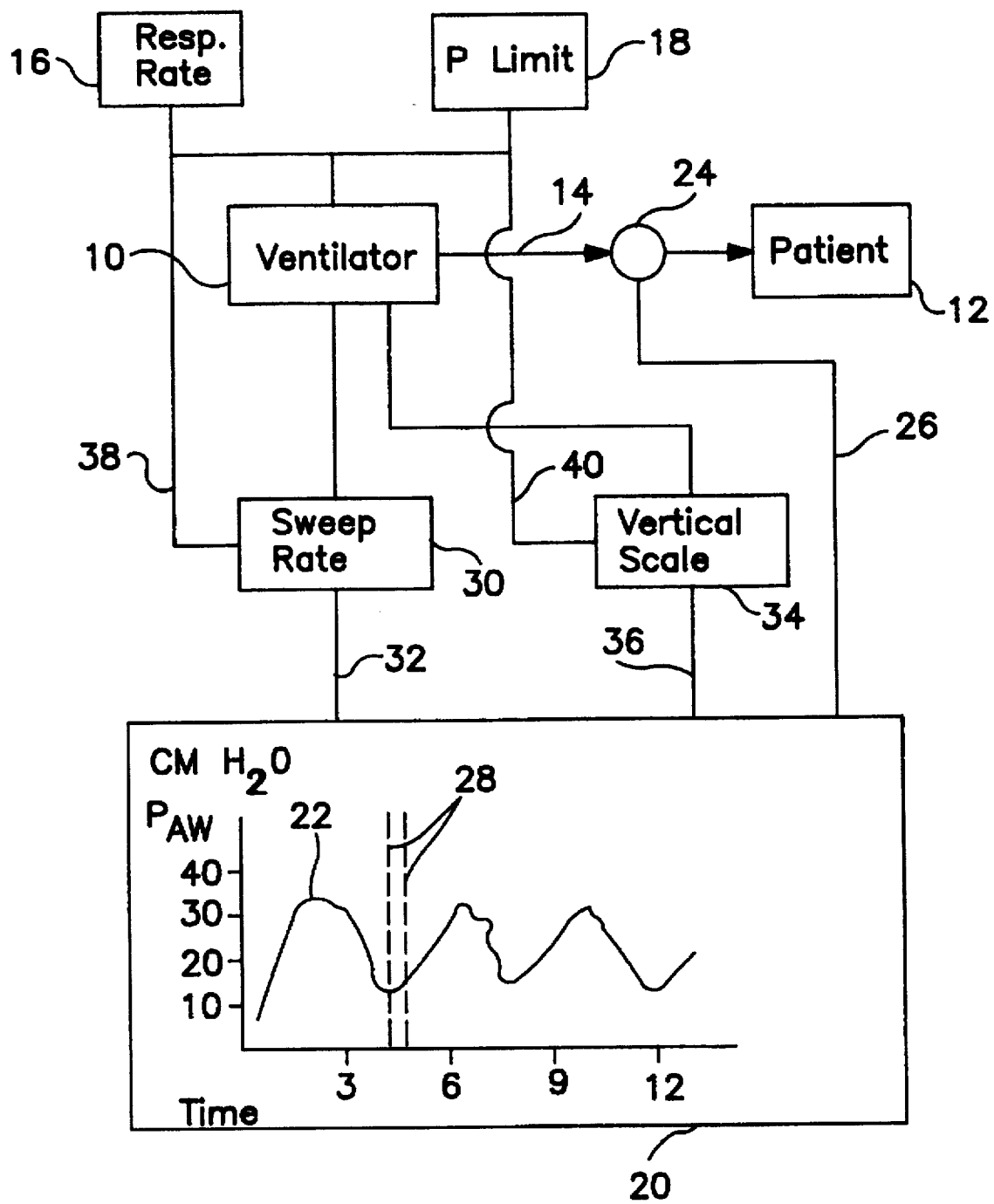

WAVEFORM DISPLAY FOR MEDICAL VENTILATOR

BACKGROUND OF THE INVENTION

This invention relates to medical ventilators and, more particularly, to an improved system for providing and displaying the pressure waveform of the gasses provided to a patient from a medical ventilator.

In general, medical ventilator systems are used to provide respiratory support and anesthesia to patients undergoing medical treatment. The primary function of the ventilator is to maintain suitable pressure and flow of gases inspired and expired by the patient. Ventilator systems which are used in the administration of anesthesia to a patient undergoing an operation may include a bellows arrangement through which anesthetic gasses are provided to the patient. Alternatively, when used in an ICU setting, the ventilator may provide flow directly to the patient.

With any use of a ventilator, however, it is very helpful for the clinician to be able to monitor certain parameters of the ventilator and its relation to the patient. Typically the ventilators therefore have displays that provide that information to the clinician as rapidly as possible and in a form that is most convenient to get needed information that is easy to understand and is relevant to the current status of the ventilator. One such display is the display of the pressure waveform, that is, the actual waveform of the pressure in the breath being provided to the patient and which is needed information for the clinician to carry out the ventilation of the patient, whether during anesthesia or in critical care ventilation.

A difficulty with such displays is that the information may be appropriately set forth for one set of data and/or conditions of the ventilator but less appropriate if those conditions change significantly. For example, when the maximum pressure to the patient is at one level, the wave form may be adequate to display the data in sufficient clarity, however, if that maximum pressure is changed by the clinician, the waveform may be too large or too small to display the new data.

It is possible for the operator to continually manually change the waveform as appropriate, however, it is inconvenient and can be missed, particularly when the clinician is busy attending to the patient or is otherwise diverted in attention. Accordingly, the waveform may or may not be the optimum form for the particular data being displayed.

Medical ventilators typically employ pressure limit features which prevent the maximum pressure at the patient's airway from exceeding a specific value. It is also desirable for a ventilator system to prompt the user to specify this maximum value at an appropriate level. This is a patient safety concern as inappropriate settings could allow the ventilator to deliver potentially harmful levels of gas volume and pressure.

SUMMARY OF THE INVENTION

The system of the present invention therefore correct the aforedescribed problem by providing an automatic control of the pressure waveform that is displayed to the clinician depending on the parameter being delivered by the ventilator. Accordingly, as one of the parameters is the respiratory rate of the ventilator, that is, the number of breaths per minute delivered to the patient, the sweep of the waveform display automatically changes to provide an appropriate sweep rate in accordance with the particular respiratory rate then being delivered by the ventilator.

In addition, another parameter of the ventilator set by the clinician is the maximum pressure in the patient circuit and, again, the height of the pressure waveform scale is adjusted automatically in accordance with the setting of that maximum pressure. In either case, the values are actually set by the clinician by selecting the setting on the ventilator, however, by choosing that setting, the ventilator automatically provides the information to the display and the waveform display is then automatically adjusted to best display the waveform. Accordingly the clinician need not make any changes to the display since that change is controlled automatically when the particular limit or parameter is selected on the ventilator.

In the particular case of the pressure limit setting, the invention can further the cause of patient safety. By tying the pressure waveform to this critical setting, the clinician's efforts to scale the pressure waveform appropriately will lead to a setting of the pressure limit at a value representative of the current pressure waveform. For example, if a certain case results in waveforms with a maximum pressure of 20 cm. $H_2O$, the clinician would be inclined to set a pressure limit of less than 40 cm. $H_2O$ so as to achieve the best waveform representation.

In summary, therefore, the present invention can be used to modify a characteristic of the display of a parameter indicative of the ventilator and/or the patient. In general, the present description utilizes a waveform as the display, however, it should be noted that the present invention is applicable to other forms of display, including a bargraph, loops or other means of displaying the data representing a particular parameter or parameters. In addition, the characteristic of the display that is described herein my be of a variety of characteristics, including vertical scale, horizontal scale, sweep rate of an erase bar or data update bar, or any other characteristic of the display that provides information to the user.

Other objects, features and advantages of the present invention will be more readily apparent from the detailed description of the preferred embodiment set forth below, taken in conjunction with the accompanying drawings.

DESCRIPTION OF THE DRAWING

The FIGURE is a block diagram of a ventilator system with a waveform display utilizing the present invention.

DESCRIPTION OF THE PREFERRED EMBODIMENT

Referring now to the FIGURE, there is shown a block diagram of a ventilator 10 having a waveform display that incorporates the present invention. In the FIGURE, the medical ventilator 10 provides ventilation to a patient 12 via a conduit 14. As stated, the ventilator 10 may be of the type used in the administration of anesthesia and therefore may include a bellows assembly intermediate the ventilator 10 and the patient 12 or, the ventilator may be of the type used in critical care situations where the ventilator directly administers to the patient.

A ventilator that is usable with the present invention is shown and described in U.S. Pat. No. 5,315,989 of Tobia and which is assigned to the present assignee and the disclosure of which is incorporated herein by reference.

Typical control of such ventilators currently on the market is the control of respiration rate, that is the rate of the cycles of the ventilator in administering breaths to the patient. The respiration rate is selected by the user and is identified as an input in block 16. That rate may be from generally 4 to 100 breaths per minute and the rate is chosen depending upon the therapy or conditions of the patient.

Another setting of conventional ventilators currently on the market and of the particular ventilator shown and described it the aforementioned U.S. Patent, is the maximum pressure in the patient airway, that is the maximum pressure that actually reaches the patient and may generally be in the range of between 12–100 cm. of $H_2O$. Again, the value is set by the user in the ventilator and that input is identified as block 18 in the FIGURE and will be referred to as the $P_{LIMIT}$.

A waveform display 20 is also provided and may be built into the ventilator 10 or provided as a separate component. The waveform display 20 is, of course, positioned so as to be convenient to the clinician and provides necessary information to that user in order for the user to properly carry out the ventilation of the patient.

Among other data and output of information on the waveform display is a waveform 22 that provides a real time indication of the pressure in the patient airway $P_{AW}$. The pressure for that waveform is provided by a pressure transducer 24 that senses the pressure in the patient airway and provides that information by means of a cable 26 to the waveform display 20. Alternately, of course, the pressure transducer 24 may provide the indication of pressure to the ventilator 10 and the ventilator may, in turn, provide the signal to the waveform display.

The waveform 22 itself is shown and is a plot of the $P_{AW}$ in cm. $H_2O$ along the vertical axis and the time along the horizontal axis. As is conventional in waveform displays, the waveform has an erase bar, indicated by the dotted lines 28 and which continually conducts a timed sweep across the waveform display 20 to update the data therein displayed. Alternatively, the sweep may continue to add new data to continually update the particular waveform rather that provide an erase function.

As an example, as new data is gathered by the pressure transducer 24, that data is continually supplied to the waveform display 20 and the data is timed to give a temporal representation of that data. As the sweep moves across the waveform display, the new data generates a new waveform and the prior waveform is erased. The rate of the sweep, that is, the number of sweeps per minute is conventionally established by a waveform sweep rate indicated by the block 30. Conventionally, the user can select the desired sweep rate and manually change it as desired to the preferred rate depending on the speed needed to continually have updated information.

As shown, the sweep rate from block 30 is communicated to the waveform display 20 by a bus 32.

In a similar manner, the vertical scale of the waveform display 20 is predetermined by a setting and is represented by the block 34 in the FIGURE. The vertical scale controls the vertical height of the particular waveform that is displayed on the waveform display 20 and, conventionally, is manually set and adjusted by the user, again depending on the particular data being displayed. The vertical scale block 34 communicates the vertical display 20 selected by means of the bus 36.

Further communication busses 38 and 40 connect, respectively, the respiratory rate input 16 with the sweep rate block 30 and the $P_{LIMIT}$ input 18 with the vertical scale block 34. As can therefore be seen, as the user inputs the ventilator 10 with desired set points of the respiratory rate, for example, the ventilator 10 changes its functioning to that respiratory rate and at the same time, the input is communicated to the sweep rate block 30 and which changes the sweep rate of the waveform 22.

That communication is accomplished without input by the user other that to select the desired respiratory rate by the input 16. The change of sweep rate of the wave form is then automatically altered to increase that sweep rate in the event a faster respiratory rate is selected by the user or, obviously, to slow down the sweep rate if a lower respiratory rate is selected.

As examples, the change in sweep rate can be made accordingly to a range of selected respiratory rates, that is, the sweep rate may be 0–15 seconds to pass through the waveform if the respiratory rate is set by the user between 4 and 25 breaths per minute. The sweep rate may be faster, i.e. 0–5 seconds where the respiratory rate is selected between 26 to 75 breaths per minute and the fastest, i.e. 0–3 seconds when the respiratory rate is set by the user to exceed 75 breaths per minute. The rate is defined above as the start time and the time the sweep has completed its movement across the display, that is, the sweep of the erase bar commences its sweep at time 0 and completes the sweep across the display in the number of seconds indicated.

Accordingly, the sweep rate is tied into and controlled by the setting made by the user of respiratory rate, the faster that rate is set, the faster the sweep rate is programmed so as to properly show all of the data in a time frame necessary for the clinician to monitor the patient.

Along the Y-axis, the vertical scale of the waveform can likewise be determined by the range of value selected by the user for the ventilator 10. Again, for example, if the user sets a low $P_{LIMIT}$, the vertical scale will be lowered so that the relatively low value of pressure can be properly displayed for the user toward the top of the vertical scale. Where the user resets the $P_{LIMIT}$ to a higher level, the vertical scale is increased so that the vertical scale reads the higher value as full scale.

As specific examples with a ventilator, if the user sets a $P_{LIMIT}$ in the range of 12 to 40 cm. $H_2O$, the y-axis range is established as –5 to 40, thus full scale is 40 cm. $H_2O$. If the user resets the $P_{LIMIT}$ to a value within the range of 41 to 60 cm. $H_2O$, the vertical scale is readjusted to –5 to 60, thus full scale is expanded to increase those possible values of the pressures in the patient airway. Finally, if the user selects a $P_{LIMIT}$ in the range of from 61 to 100 cm. $H_2O$, the scale limits change to –5 to 100 cm. $H_2O$ so that those values are included on the waveform in the proper perspective.

As explained, the vertical scale also conveys to the clinician information as to whether the appropriate $P_{LIMIT}$ has been selected for the particular patient.

As can be seen therefore, the sweep rate and the vertical scale of the waveform display 20 change automatically, without user intervention, when the user selects certain settings for the ventilator 10 and the scale thus provides the needed information in a manner best designed to have the data displayed to the user.

Again, however, the specific characteristic of the display that is modified can be a variety of characteristics, that is, the horizontal scale or other characteristic may be changed as the parameter measured changes or other characteristic. Also, while a waveform is the preferred display, the display may be a bargraph, loop, or other curve indicative of a desired parameter of the ventilator and/or the patient that is displayed to keep the clinician informed as to the status of the ventilator and/or the patient.

While the present invention has been set forth in terms of a specific embodiment, it will be understood that the waveform display algorithm herein disclosed may be modified or altered by those skilled in the art to other configurations. Accordingly, the invention is to be broadly construed and limited only by the scope and spirit of the claims appended hereto.

We claim:

1. A system for controlling a waveform display of a parameter of a breathing gas delivered from a medical ventilator to a patient through a conduit, said system comprising an input device to enable a user to send a signal to the ventilator to establish a desired parameter in the gas delivered by the ventilator to the patient, a sensor for sensing in the gas delivered to the patient the desired parameter established by the user with said input device, said sensor providing a signal representative of such sensed parameter, a display for displaying the sensed parameter in the shape of a waveform, said display including an erase bar that erases old data and enters new data to modify the waveform as said erase bar moves across said display, and a processor to receive said signal from said input device to modify the sweep rate of the said erase bar in response to the desired parameter established by the user.

2. A system as defined in claim 1 wherein said sweep rate changes in accordance with a time related parameter established by the user.

3. A system as defined in claim 2 wherein said time related parameter is breaths per minute of the gas delivered to the patient by the ventilator.

4. A system as defined in claim 3 wherein said sweep rate is increased when the user establishes an increase in the breaths per minute delivered by the ventilator to the patient by means of said input device.

5. A system for controlling a waveform display of a parameter of a breathing gas delivered from a medical ventilator to a patient through a conduit, said system comprising an input device to enable a user to send a signal to the ventilator to establish a desired parameter in the gas delivered by the ventilator to the patient, a sensor for sensing in the gas delivered to the patient the desired parameter established by the user with said input device, said sensor providing a signal representative of such sensed parameter, a display for displaying the sensed parameter in the shape of a waveform having a vertical scale, and a processor to receive said signal from said input device to modify the vertical scale of the waveform in response to the desired parameter established by the user.

6. A medical ventilator system for delivering breaths to a patient and monitoring a parameter of the breaths, said system comprising a medical ventilator, an airway for delivering gas from said ventilator to the patient, said ventilator having means to manually set a parameter indicative of a desired parameter in the gas delivered to the patient, a sensor in said airway for sensing the desired parameter, a display for displaying a waveform having waveform having a vertical scale and having the sensed parameter as an input to form said waveform and a processor for modifying the vertical scale of said waveform to increase and decrease the vertical scale depending on the parameter manually set in said ventilator.

7. A medical ventilator as defined in claim 6 wherein said characteristic is the sweep rate of an erase bar that travels across said waveform display to erase old data and to input new data to reform said waveform.

8. A medical ventilator as defined in claim 7 wherein the parameter manually set in said ventilator is breaths per minute delivered to the patient.

9. A medical ventilator as defined in claim 8 wherein said sweep rate increases as said set parameter increases.

10. A system as defined in claim 5 wherein said sensor is located in the conduit and senses pressure of the breathing gas delivered to the patient.

11. A system as defined in claim 10 wherein said vertical scale changes with changes in the maximum pressure established by the user for the gas delivered to the patient.

12. A system as defined in claim 11 wherein said vertical scale is decreased where the user decreases the maximum pressure delivered to the patient with said input device.

13. A medical ventilator system for delivering breaths to a patient and monitoring a parameter of the breaths, said system comprising a medical ventilator, an airway for delivering gas from said ventilator to the patient, said ventilator having means to manually set a parameter indicative of a desired parameter in the gas delivered to the patient, a sensor in said airway for sensing the pressure in said airway of the gas delivered by said ventilator to the patient, a display for displaying a waveform representing the pressure sensed by said pressure sensor with respect to time, and a processor for modifying the vertical scale of said waveform to increase and decrease the vertical scale depending on the parameter manually set in said ventilator.

* * * * *